Jan. 15, 1946. J. W. NICHOLSON Plant Pat. 670
PEACH TREE
Filed Dec. 27, 1944
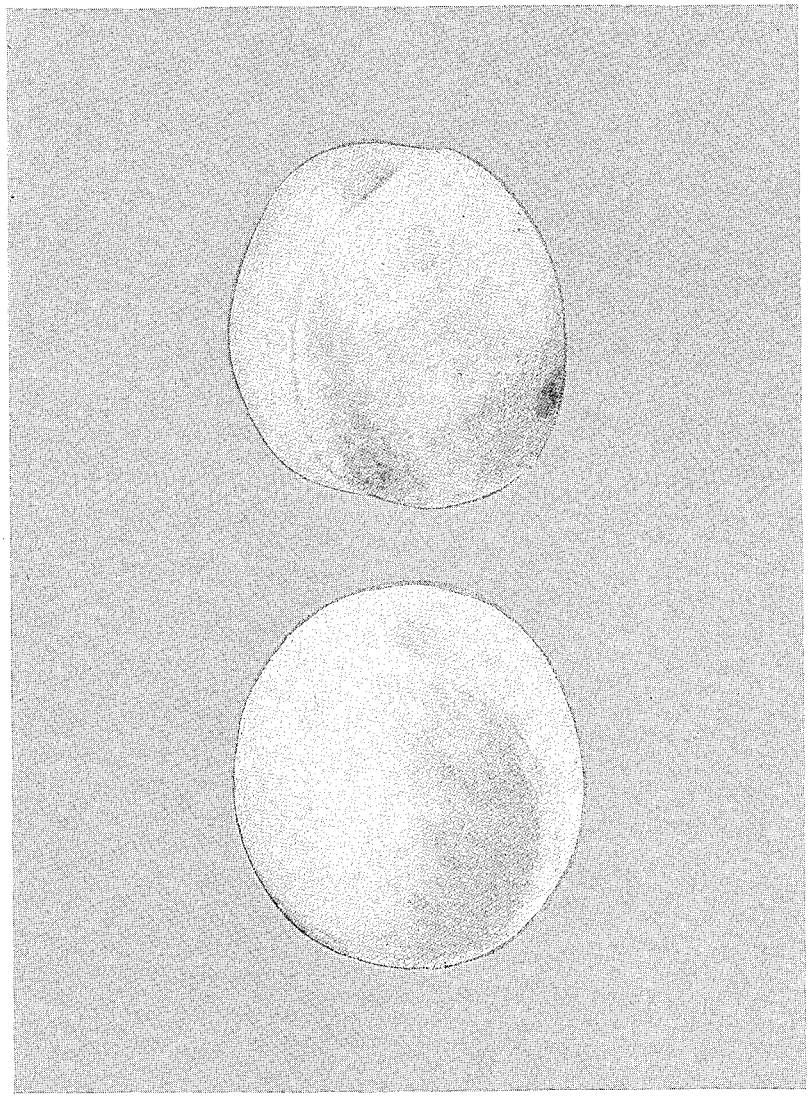
Inventor
J. W. Nicholson.
By Robbins & Robbins
Attorneys Patented Jan. 15, 1946

Plant Pat. 670

UNITED STATES PATENT OFFICE

670

PEACH TREE

John W. Nicholson, Ash Grove, Mo., assignor to Stark Bro's Nurseries and Orchards Company, Louisiana, Mo., a corporation of Missouri Application December 27, 1944, Serial No. 569,984

1 Claim. (Cl. 47—62)

The present invention relates to a new and distinct variety of peach tree which was originated by me by the planting of a seed, after hand pollinating, of the variety "Greensboro" with a very hardy unnamed seedling.

This hybridizing has resulted in a greatly improved variety characterized as to novelty by the hardiness of bud. After extensive tests of this new variety, it has been proved to be far more consistently hardy than "Greensboro," which itself is noted for hardiness, and, moreover, constantly the most hardy variety among a great number of standard and test varieties grown under comparable conditions.

This hardy characteristic is particularly important in an early variety such as this new variety is, since it begins to ripen about five days after "Red Bird" immediately following "Early Rose" with "Greensboro," and a week to ten days ahead of "Golden Jubilee." The fruit is shaped similarly to that of the Greensboro variety, but is more highly colored, and very superior in eating and handling qualities.

The present peach is a white cling of good quality and an almost certain cropper. From the commercial standpoint, it is especially adapted to home and road-side market orchardists because the ripening period extends over a period of three to four weeks.

Asexual reproduction shows that these characteristics hold true through succeeding propagations.

The following is a detailed description of this new peach from observations of specimen trees grown in the vicinity of Atlas, Pike County, Illinois, color terminology being in accord with Ridgway's color standard, except where used in the obvious dictionary sense.

Tree: Medium in size; vigorous; open and spreading with normal orchard training; tends toward round top if unpruned; very hardy; productive; regular bearer.

*Trunk.*—Medium stout; smooth.

*Branches.*—Medium stout; smooth; red. *Lenticels*—very numerous, medium in size.

*Leaves.*—Length four to six inches; width one to one and three-quarters inches; medium in size; lanceolate, acutely pointed; medium thick; medium green; smooth. *Petiole*—medium in length and thickness. *Glands*—average of two; mostly opposite; medium in size; reniform; free; non-pubescent.

Flowers: Time is variable depending upon season, but for the season of 1944, April 20th to May 10th, about with average of peach varieties in this location.

*Color.*—Pale Amaranth Pink, petals grading into deep Rose color at base. *Stamen filaments*—Amaranth Purple.

Fruit: Described July 20, 1944, at eating ripe stage of maturity.

*Size.*—Axial diameter—2.4 inches; transverse in suture plane—2.3 inches; at right angles to suture plane—2.2 inches.

*Form.*—Fairly uniform; unsymmetrical; globose; oblate; slightly compressed; sides unequal. *Suture*—distinct; shallow, becoming deeper near tip and beyond; has slight marked depression beyond pistil point. *Ventral surface*—rounded. *Cavity*—rounded; abrupt; elongated in suture plane with suture showing on both sides in some specimens; deep; narrow; no markings. *Apex*—recurved; depressed; pistil point a dot. *Stem*—short; stout; pubescent; strong.

*Skin.*—Medium in thickness; tough; tenacious to flesh. *Color*—Pomegranate Purple, blushed and streaked on sunny side over Light Orange Yellow ground color.

*Flesh.*—*Color*—Massicot Yellow; clear Dull Green Yellow near pit. Juice moderate; firm; meaty, melting; fibers few; ripens fairly evenly; flavor mild, delicate, ambrosia-like; aroma distinct; eating quality good.

Stone: Cling; small, 1.3 inches by 1 inch by .7 inch; broadly ovate; bulges on one side; acute at apex; sides unequal; surface furrowed throughout; ridges rounded.

Use: Local; culinary; canning.

Keeping quality: Good.

Resistance to insects and disease: Good.

Shipping quality: Good.

I claim:

A new and distinct variety of white clingstone peach tree, characterized as to novelty by its great hardiness, more highly colored skin of its fruit when compared with its seed parent, firmness of the flesh and superior eating quality of its fruit, and its early and extended ripening period particularly adapting it to home and road-side orchard usage, substantially as shown and described.

JOHN W. NICHOLSON.